(12) United States Patent
Chang et al.

(10) Patent No.: US 7,963,512 B2
(45) Date of Patent: Jun. 21, 2011

(54) SYNCHRONOUS APPARATUS

(75) Inventors: Chih-Kuang Chang, Taipei Hsien (TW); Sen Zhang, Shenzhen (CN)

(73) Assignees: Hong Fu Jin Precision Industry (ShenZhen) Co., Ltd., Shenzhen, Guangdong Province (CN); Hon Hai Precision Industry Co., Ltd., Tu-Cheng, New Taipei (TW)

( * ) Notice: Subject to any disclaimer, the term of this patent is extended or adjusted under 35 U.S.C. 154(b) by 481 days.

(21) Appl. No.: 12/198,341

(22) Filed: Aug. 26, 2008

(65) Prior Publication Data

US 2009/0251692 A1 Oct. 8, 2009

(30) Foreign Application Priority Data

Apr. 3, 2008 (CN) .......................... 2008 1 0300837

(51) Int. Cl.
*B23Q 1/25* (2006.01)
(52) U.S. Cl. .......... 269/55; 269/329; 269/903; 29/281.1
(58) Field of Classification Search .................. 269/55, 269/136, 138, 903, 58, 329, 909; 29/281, 29/1
See application file for complete search history.

(56) References Cited

U.S. PATENT DOCUMENTS

| | | | | |
|---|---|---|---|---|
| 5,263,696 A | * | 11/1993 | Frye | 270/45 |
| 6,964,092 B1 | * | 11/2005 | Lorenz et al. | 29/721 |
| 7,771,248 B2 | * | 8/2010 | Vianello et al. | 451/5 |
| 2006/0160250 A1 | * | 7/2006 | Bonassar et al. | 438/1 |
| 2009/0251692 A1 | * | 10/2009 | Chang et al. | 356/244 |
| 2010/0071521 A1 | * | 3/2010 | Hadaway et al. | 83/76.1 |

* cited by examiner

*Primary Examiner* — Lee D Wilson
(74) *Attorney, Agent, or Firm* — Clifford O. Chi

(57) ABSTRACT

A vision measuring machine includes a workbench, a support mounted to the workbench, a moving member movably mounted to the support, two fixing portions and a lens respectively fixed to the moving member, a group of pulleys fixed to the support, two mounting members each including at least one pulley fixed to the workbench, a rail fixed between the fixing members, a sliding member for fixing a backlight module, and a cord for driving the sliding member. One end of the cord is fixed to one of the fixing portions. The opposite end of the cord rounds all of the corresponding pulleys, the rail, and the sliding member, and last is fixed to the other fixing portion. When the moving member with the lens is driven, the backlight module is driven together with the lens by the cord.

9 Claims, 5 Drawing Sheets

SYNCHRONOUS APPARATUS

BACKGROUND

1. Field of the Invention

The present invention relates to synchronous apparatuses. The invention particularly relates to a synchronous apparatus for driving a lens and a backlight module of a vision measuring machine to move synchronously.

2. Description of Related Art

Vision measuring machines are often used during assembly to check parameters of workpieces, which can potentially save time and labor. However, a lens of the vision measuring machine and a backlight module cannot move synchronously, so the backlight module must be kept lit throughout the work process to ensure proper lighting during image capture, leading to energy waste.

What is needed, therefore, is to provide a synchronous apparatus which drives a lens and a backlight module to move synchronously.

DETAILED DESCRIPTION OF THE EMBODIMENTS

Figure 1:
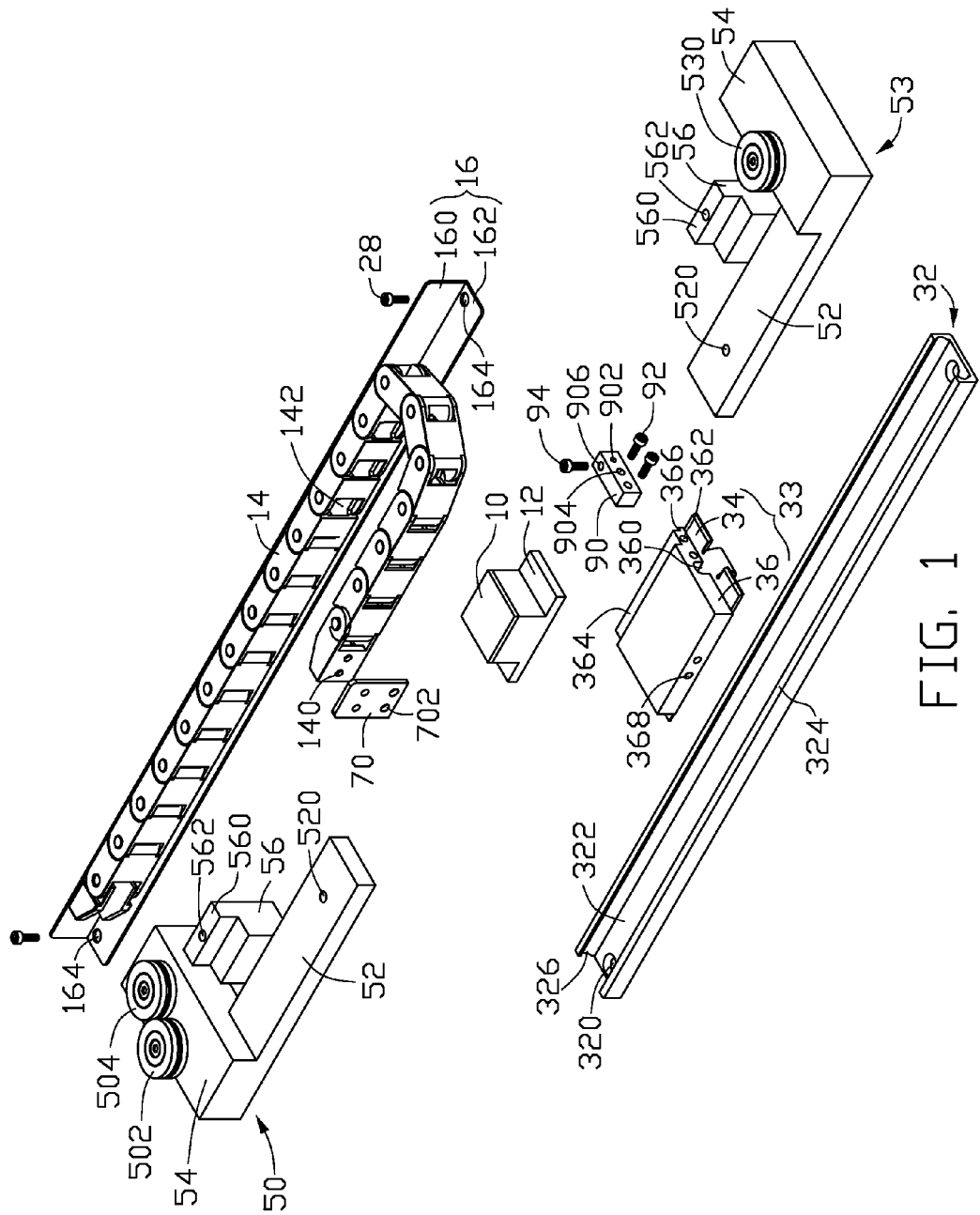
FIG. 1 is an exploded, isometric view of an embodiment of a synchronous apparatus, shown without a cord, the synchronous apparatus including a chain and a bracket.
Figure 2:
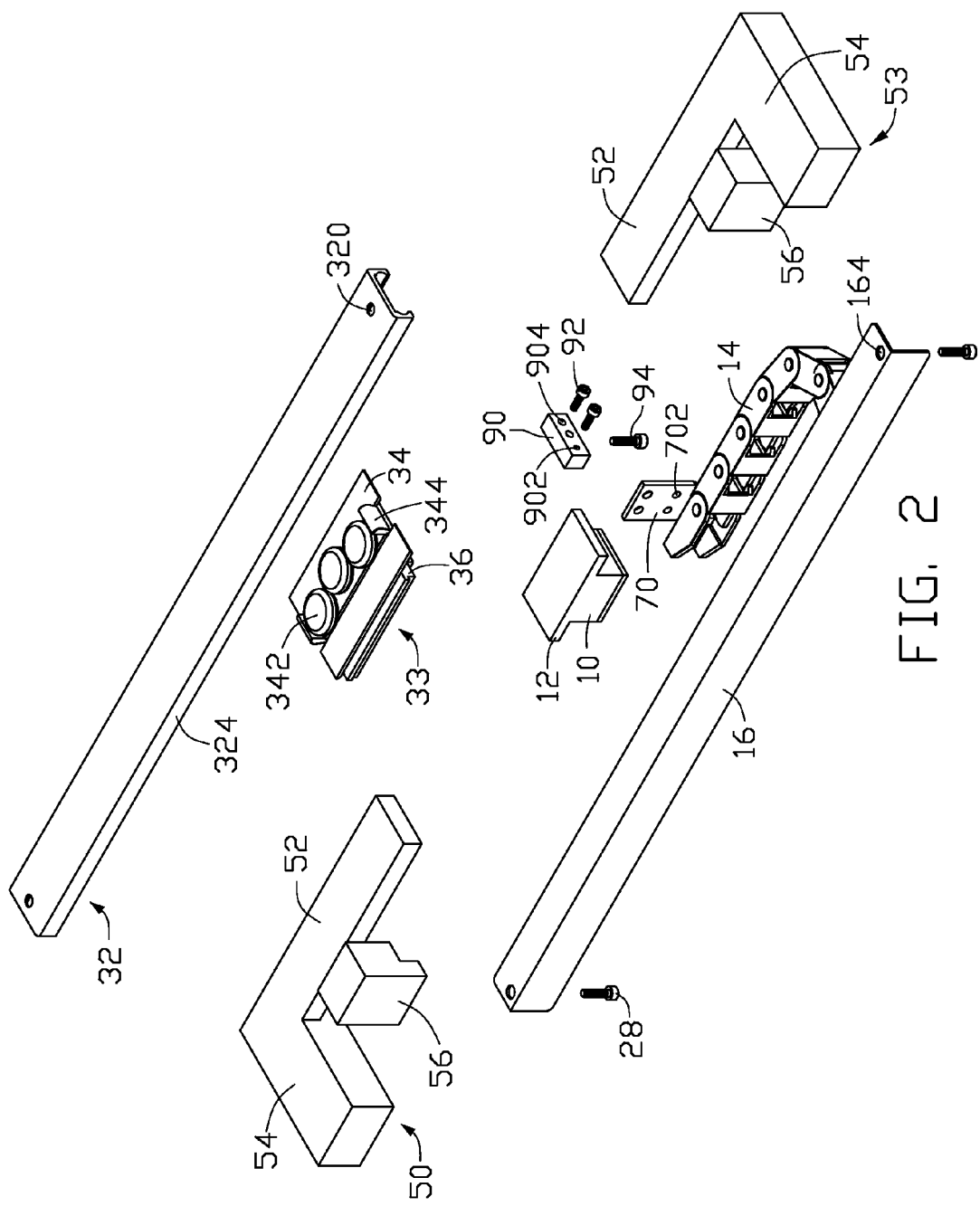
FIG. 2 is a partial, exploded, isometric view of the synchronous apparatus of FIG. 1, but from a different aspect.
Figure 3:
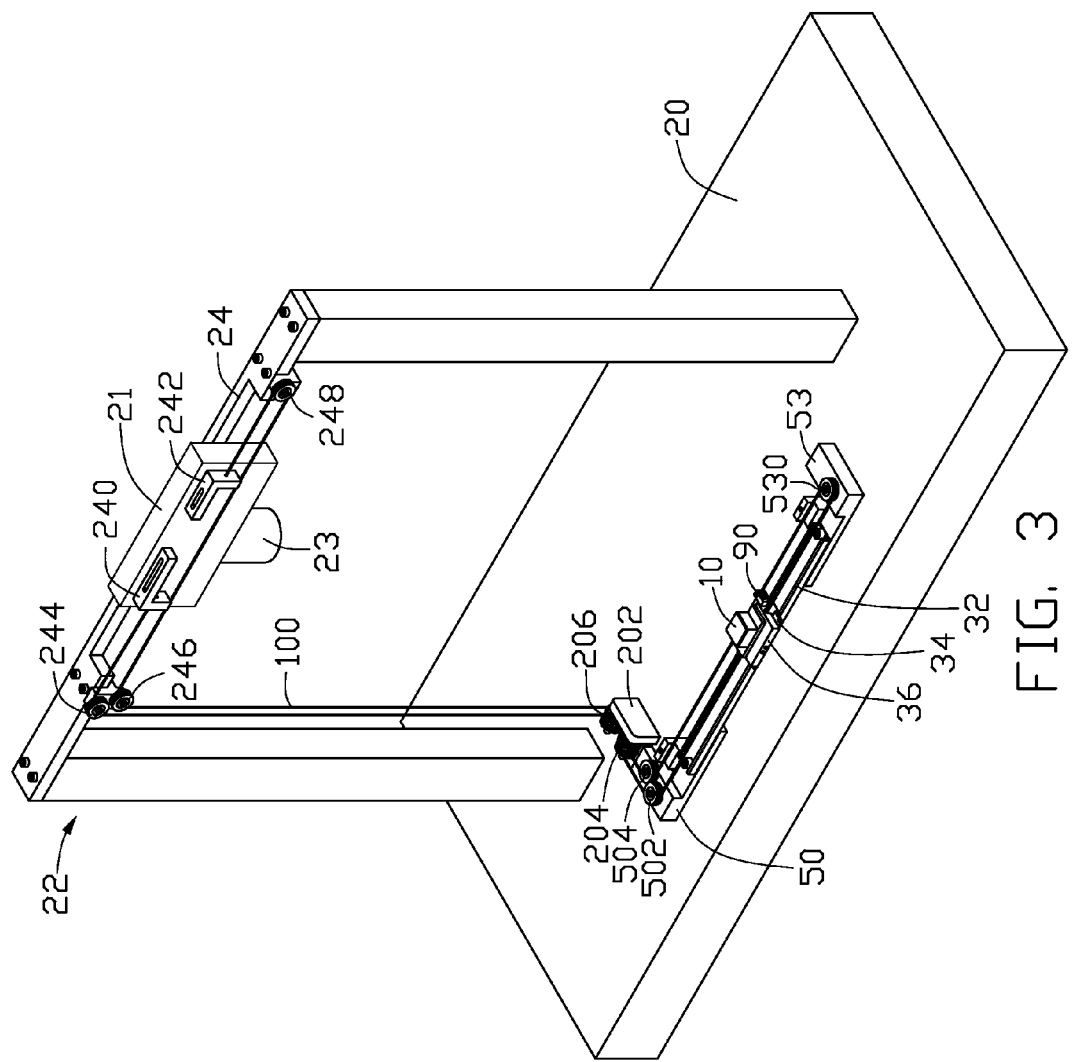
FIG. 3 is an assembled, isometric view of the synchronous apparatus of FIG. 1 and partial members of a vision measuring machine shown with the cord, but without the chain and the bracket.

Referring to FIG. 1 to FIG. 3, an embodiment of a synchronous apparatus is used for driving a lens 23 and a backlight module 10 of a vision measuring machine to move synchronously. The vision measuring machine includes a workbench 20, a support 22 mounted to the workbench 20, and a moving member 21. The support 22 includes two parallel poles perpendicularly mounted to the workbench 20, and a crossbeam 24 parallel to the workbench 20 and connecting tops of the poles. The moving member 21 is slidably mounted to the crossbeam 24. The lens 23 is fixed to the moving member 21 and facing the workbench 20. A first fixing portion 240 and a second fixing portion 242 are fixed to the moving member 21. The first and second fixing portions 240, 242 and the lens 23 are moved together with the moving member 21.

The synchronous apparatus includes a rigid chain 14, a bracket 16 supporting the chain 14, a rail 32, a positioning member 202, a sliding member 33 slidable along the rail 32, a first mounting member 50, a second mounting member 53, a locking element 70, a securing member 90, a first pulley 244, a second pulley 246, a third pulley 248, and a cord 100. Two cylindrical sleeves 204, 206 extend from the positioning member 202.

The backlight module 10 is connected to a power supply by a wire. Two protrusions 12 extend from opposite sidewalls of the backlight module 10.

The rigid chain 14 defines a receiving rooms 142 configured for receiving the wire. One end of the rigid chain 14 defines two fixing holes 140, and the other opposite end of the chain 14 forms a fixing end. The bracket 16 includes a first supporting potion 160 and a second supporting portion 162 perpendicularly extending from an edge of the first supporting portion 160. Each end of the second supporting portion 162 defines a screw hole 164.

A cross section of the rail 32 is substantially U-shaped. The rail 32 includes a board 322 and two opposite guide portions 324 substantially perpendicularly extending from opposite edges of the board 322. Each end of the board 322 defines a screw hole 320. An inside wall of each guide portion 324 defines an arc-shaped slot 326.

The sliding member 33 includes a sliding element 34 and a connecting element 36 fixed to a top of the sliding element 34. Three round sliding portions 342 are triangularly arranged on a bottom of the sliding element 34 and configured for sliding in the arc-shaped slots 326. Two tabs 344 extend down from opposite ends of the sliding element 34 and configured for protecting the sliding portions 342. A bottom of the connecting element 36 defines a longitudinal groove 360 through opposite end surfaces. One end surface of the connecting element 36 defines two screw holes 362 at a side of the groove 360. A step portion 364 extends from a first side of the connecting element 36 such that a top of the step portion 364 is lower than a top of the connecting element 36. A support board 366 extends from a side of the step portion 364 such that a top of the support board 366 is lower than a top of the step portion 364. A second opposite side of the connecting element 36 defines two fixing holes 368.

Each of the first and second mounting members 50, 53 includes a mounting portion 54, an arm 52 perpendicularly extending from a side at an end of the mounting portion 54, and a connecting body 56 mounted to the side of the arm 52, adjacent an opposite end of the mounting portion 54. The arm 52 defines a screw hole 520 in an opposite end of the arm 52. A connecting part 560 defining a fixing hole 562 in a top extends up from a top of the connecting body 56. A fourth pulley 502 and a fifth pulley 504 are mounted to a top of the mounting portion 54 of the first mounting member 50. A sixth pulley 530 is mounted to a top of the mounting portion 54 of the second mounting member 53.

Four fixing holes 702 are defined on a surface of the locking member 70.

The securing member 90 defines a through hole 902 extending through opposite sides of the securing member 90, and two screw holes 904 adjacent the through hole 902. A top of the securing member 90 defines a fixing hole 906 communicating with the through hole 902.

Figure 4:
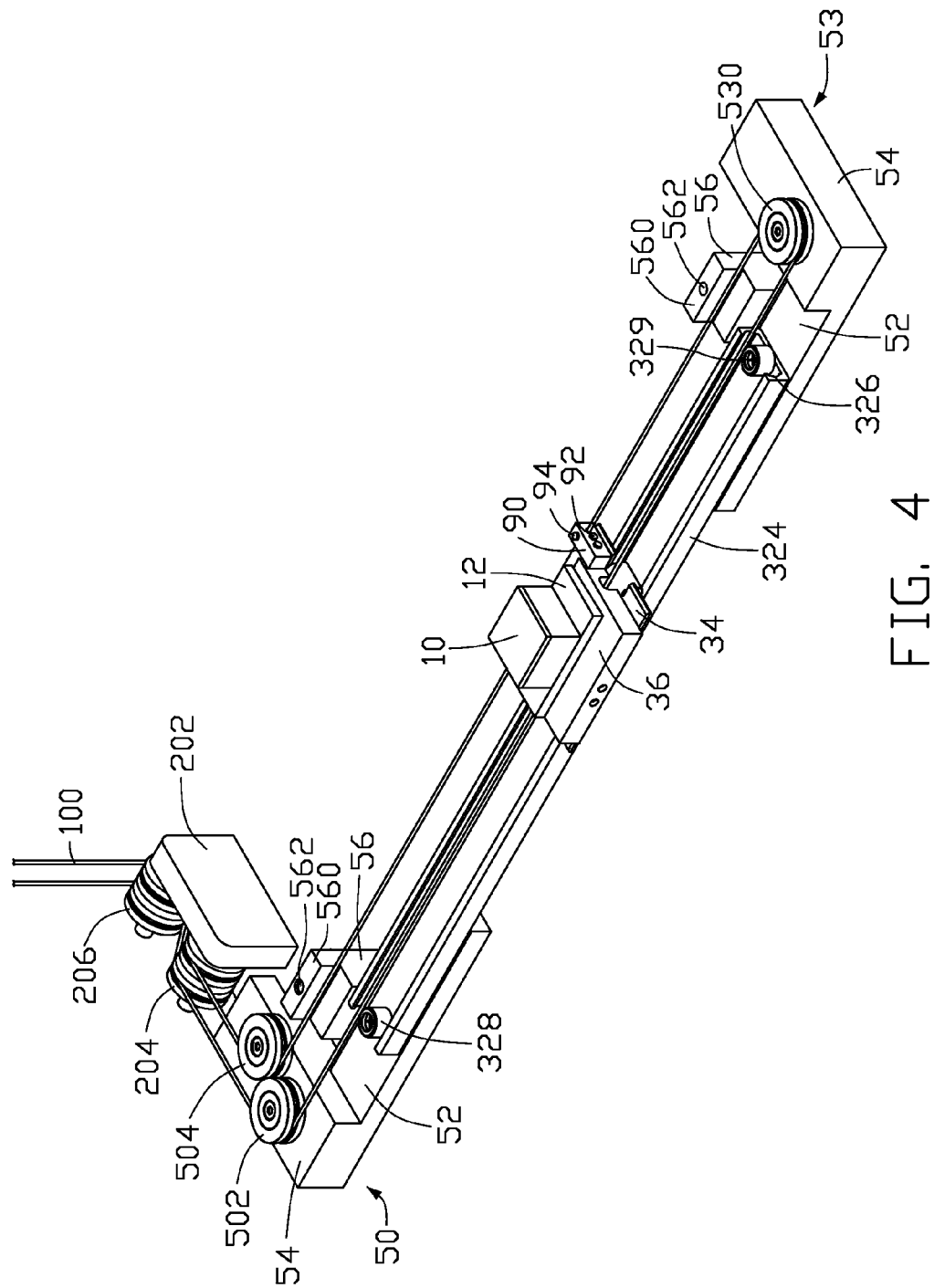
FIG. 4 is a partial, enlarged view of synchronous apparatus of FIG. 3.
Figure 5:
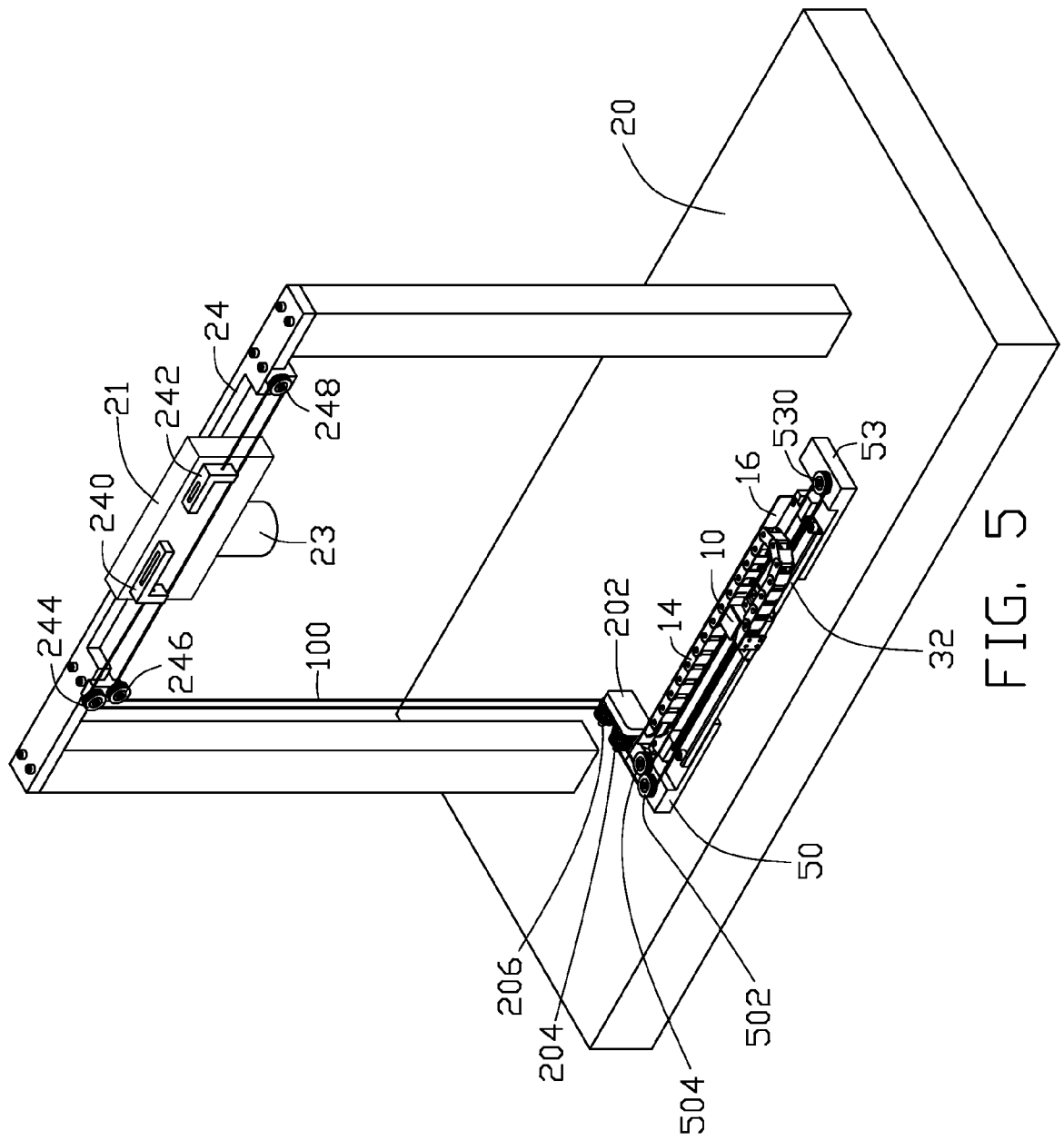
FIG. 5 is an assembled, isometric view similar to FIG. 3, but shown with the chain and the bracket.

Referring also to FIGS. 4 and 5, the sliding portions 342 of the sliding member 34 are mounted to the rail 32, and corresponding edges of the sliding portions 342 are slidably received in the slots 326. The first and second pulleys 244, 246 are fixed to a first end of the crossbeam 24, and the third pulley 248 is fixed to a second end of the crossbeam 24. The positioning member 202 is mounted to the workbench 20 below the first end of the crossbeam 24, and adjacent to one of the poles of the support 22, with the sleeves 204, 206 facing the pole. The first mounting member 50 is mounted on the workbench 20 at a side of the positioning member 202, with the mounting portion 54 adjacent to the positioning member 202. The second mounting member 53 is mounted on the workbench 20 adjacent to the other pole of the support 22. The first and second mounting member arms 52 are aligned facing each other. A screw 328 is extended through the screw hole 320 of one end of the rail 32, and threadedly engaged in the screw hole 520 of the first fixing member 50 to fix the end of the rail 32 to the first mounting member arm 52. The sixth pulley 530 of the second mounting member 53 is in alignment with the fourth pulley 502 of the first mounting member 50. A screw 329 is inserted through the screw hole 320 of the other end of the rail 32, and threadedly engaged in the screw hole 520 of the second fixing member 53 to fix the other end of the rail 32 to the second mounting member arm 52. Two screws 92 are passed through the screw holes 904 of the securing member 90, and screwed into the screw holes 362 to fix the securing member 90 to the connecting element 36. The through hole 902 of the securing member 90 is defined above the support board 366.

One end of the cord 100 is fixed to the first fixing portion 240. The cord 100 runs in the order described, through a side of the first pulley 244, a bottom of the cylinder sleeve 206, a top of the cylinder sleeve 204, a side of the fourth pulley 502, the rail 32, the groove 360, a side of the sixth pulley 530, the through hole 902, a side of the fifth pulley 504, the top of the cylinder sleeve 204, the bottom of the cylinder sleeve 206, sides of the second and third pulleys 246, 248. The other end of the cord 100 is fixed to the second fixing portion 242. A screw 94 is screwed into the fixing hole 906 to abut against the cord 100 firmly, such that the cord 100 may be fixed to the securing member 90. The protrusions 12 of the backlight module 10 are fixed to the top surface of the connecting element 36 adjacent to the step portion 364 via screws (not shown).

Two screws 28 are screwed into the screw holes 164 of the bracket 16 and the fixing holes 562 of the first and second mounting members 50, 53, so that two ends of the bracket 16 are fixed to the first and second mounting members 50, 53. Accordingly, the support board 366 and the corresponding end of the securing member 90 are below the second supporting portion 162 of the bracket 16. The corresponding sidewall of the backlight module 10 resists against a distal edge of the second supporting portion 162. The wire of the backlight module 10 is received in and passed through the receiving room 142 of the rigid chain 14. The rigid chain 14 is located on the second supporting portion 162 and between a side of the backlight module 10 and the first supporting portion 160. The fixing end of the rigid chain 14 is fixed to an end of the first supporting portion 160. The other end of the rigid chain 14 is bent to an opposite side of the backlight module 10, and is located on a top of a corresponding guide portion 324. Two screws are screwed into two of the fixing holes 702 and the fixing holes 140 to fix the rigid chain 14 to the locking member 70. Two screws are screwed into the fixing holes 368 and the other two fixing holes 702 of the fixing element 70 to fix the locking member 70 to the connecting element 36.

In use, the screw 94 is rotated to disengage from the fixing hole 906 of the securing member 90, so that the cord 100 can pass freely in the groove 360 of the connecting element 36. The connecting element 36 is adjustably moved with the backlight module 10 to align the backlight module 10 with the lens 23 mounted to the moving member 21. The screw 94 is then rotated to engage in the fixing hole 906 to firmly abut against the cord 100, thereby fixing the cord 100 to the securing member 90. A circuit connected to the backlight module 10 may be turned on to light the backlight module 10.

The moving member 21 may be moved with the lens 23, the first and second fixing portions 240, 242, and the cord 100. Accordingly, the securing member 90 is moved together with the cord 100. The backlight module 10, the sliding member 33, and the securing member 90 are fixed together, so that the backlight module 10 moves with the cord 100 and movement of the backlight module 10 is synchronized with movement of the lens 23.

In other embodiments of the invention, the securing member 90 may be omitted and the connecting element 36 defines a through hole neighboring the groove 360. The cord 100 may be passed through the through hole directly. A top of the connecting element 36 defines a fixing hole communicating with the through hole. A screw may be screwed into the through hole to abut against the cord 100, and firmly fix the cord 100 to the connecting element 36.

It is believed that the present embodiments and theirs advantages will be understood from the foregoing description, and it will be apparent that various changes may be made thereto without departing from the spirit and scope of the invention or sacrificing all of its material advantages, the examples hereinbefore described merely being preferred or exemplary embodiments.

What is claimed is:
1. A vision measuring machine, comprising:
a workbench;
a support mounted to the workbench;
a moving member movably mounted to the support;
a lens mounted to the moving member and facing the workbench;
a first pulley mounted to a first end of the support;
a second pulley mounted to the first end of the support
a third pulley mounted to a second end of the support;
a first mounting member mounted to the workbench adjacent the first end of the support;
a fourth pulley mounted to the first mounting member;
a fifth pulley mounted to the first mounting member
a second mounting member mounted to the workbench adjacent the second end of the support, the second mounting member being aligned with the first mounting member and facing the first mounting member;
a sixth pulley mounted to the second mounting member;
a rail mounted between the first and second mounting members;
a sliding member slidably mounted to the rail;
a backlight module fixed to the sliding member; and
a cord passing through the pulleys and the sliding member, wherein opposite ends of the cord are mounted to the moving member to form a closed loop; the cord is configured for sliding along the pulleys and the sliding member to synchronously adjust the lens and the backlight module when the cord is fixed to the sliding member.

2. The vision measuring machine of claim 1, wherein the rail has a substantially U-shaped cross section;
the rail comprises a board and two opposite guide portions substantially perpendicularly extending from opposite edges of the board;
two slots are defined in inside walls of the guide portions;
the sliding member comprises at least one sliding portions located at a bottom;
edges of the at least one sliding portions are slidably received in the two slots.

3. The vision measuring machine of claim 2, wherein the sliding member further comprise a sliding element and a connecting element fixed to the sliding element;
the backlight module is mounted to the connecting element;
the sliding portions are mounted to the sliding element.

4. The vision measuring machine of claim 3, further comprising a securing member mounted to an end of the connecting element, wherein the connecting element defines a groove;

the securing member defines a through hole configured for the cord passing therethrough, and a fixing hole communicating with the through hole;

the cord passing through the fourth pulley is passed through the groove, and then is passed through the sixth pulley;

the cord passed through the sixth pulley is passed through the through hole of the securing member;

a screw is screwed into the fixing hole of the securing member for firmly abutting against the cord for fixing the cord to the securing member.

5. The vision measuring machine of claim 3, wherein the first and second mounting members each comprises an arm fixed to an end of the rail.

6. The vision measuring machine of claim 5, wherein the first and second mounting members each comprise a mounting portion extending from the corresponding arm;

the fourth and fifth pulleys are both fixed to the mounting portion of the first mounting member;

the sixth pulley is fixed to the mounting portion of the second mounting member.

7. The vision measuring machine of claim 1, further comprising a rigid chain and a bracket configured for fixing and supporting the rigid chain, wherein an end of the rigid chain is fixed to the bracket and an opposite end of the rigid chain is bent towards and fixed to the sliding member.

8. The vision measuring machine of claim 7, wherein each of the first and second mounting members comprise a connecting body;

each end of the support is fixed to a connecting body.

9. The vision measuring machine of claim 1, further comprising a positioning member mounted to the workbench facing the first end of the support, and two cylinder sleeves extending from the positioning member; wherein the cord extended from the first pulley is rounded through the cylinder sleeves, sides of the forth pulley, and then sixth pulley;

the cord extended from the sixth pulley is passed through the sliding member, and then is rounded through the cylinder sleeves;

the cord extended from the cylinder sleeves is rounded through sides of the second and third pulleys.

* * * * *